US012280195B2

(12) United States Patent
Badhwar et al.

(10) Patent No.: US 12,280,195 B2
(45) Date of Patent: Apr. 22, 2025

(54) EXPANDABLE PERCUTANEOUS CANNULA

(71) Applicants: University of Pittsburgh—Of the Commonwealth System of Higher Education, Pittsburgh, PA (US); Ri.MED Foundation, Palermo (IT)

(72) Inventors: Vinay Badhwar, Washington, PA (US); Antonio D'Amore, Pittsburgh, PA (US); Daniel McKeel, Pittsburgh, PA (US); William R. Wagner, Gibsonia, PA (US)

(73) Assignees: University of Pittsburgh—Of the Commonwealth System of Higher Education, Pittsburgh, PA (US); Ri.MED Foundation, Palermo (IT)

( * ) Notice: Subject to any disclaimer, the term of this patent is extended or adjusted under 35 U.S.C. 154(b) by 960 days.

(21) Appl. No.: 16/485,240

(22) PCT Filed: Feb. 12, 2018

(86) PCT No.: PCT/US2018/017795
§ 371 (c)(1),
(2) Date: Aug. 12, 2019

(87) PCT Pub. No.: WO2018/148646
PCT Pub. Date: Aug. 16, 2018

(65) Prior Publication Data
US 2019/0365981 A1    Dec. 5, 2019

Related U.S. Application Data

(60) Provisional application No. 62/458,234, filed on Feb. 13, 2017.

(51) Int. Cl.
*A61M 1/36* (2006.01)

(52) U.S. Cl.
CPC ......... *A61M 1/3659* (2014.02); *A61M 1/3666* (2013.01); *A61M 1/3673* (2014.02)

(58) Field of Classification Search
CPC .............. A61M 1/3659; A61M 1/3666; A61M 1/3673; A61M 1/365; A61M 25/0017
See application file for complete search history.

(56) References Cited

U.S. PATENT DOCUMENTS 3,995,623 A     12/1976  Blake et al.
4,804,163 A  *  2/1989   Yang ........................ E03B 9/02
                                                                137/460

(Continued)

FOREIGN PATENT DOCUMENTS

WO      2014031362 A1      2/2014
WO      2016128840 A1      8/2016
WO      WO-2018200643 A1 * 11/2018 ............. A61F 2/042

OTHER PUBLICATIONS

Gasparyan, "Total Autologous Mitral Valve Reconstruction: An Experimental Study", CTSNet, 2015, https://www.ctsnet.org/article/total-autologous-mitral valve-reconstruction-experimental study, Abstract.

(Continued)

*Primary Examiner* — Rebecca E Eisenberg
*Assistant Examiner* — Kate Elizabeth Strachan
(74) *Attorney, Agent, or Firm* — Klarquist Sparkman, LLP

(57) ABSTRACT

Provided herein is a percutaneous expandable venous cannula device, and related methods. The device is easily inserted, for example, using standard Seldinger technique via the right internal jugular. The device includes multiple, multi-holed limbs that softly fill, e.g., the right atrium to facilitate complete drainage, enable retraction of the chamber in surgery, and mitigate suction occlusion, filling the entire atrium and allowing for efficient and rapid emptying (Continued)

of the chamber. In aspects, the device facilitates minimally-invasive aortic or mitral valve surgery with single placement via the right internal jugular as the sole cannula needed for full support.

18 Claims, 5 Drawing Sheets

(56) References Cited

U.S. PATENT DOCUMENTS

| | | | |
|---|---|---|---|
| 4,808,163 A | 2/1989 | Laub | |
| 4,960,424 A | 10/1990 | Grooters | |
| 6,009,877 A * | 1/2000 | Edwards | A61B 18/1206 606/41 |
| 6,270,490 B1 * | 8/2001 | Hahnen | A61M 25/00 604/509 |
| 6,673,042 B1 * | 1/2004 | Samson | A61M 29/02 606/198 |
| 7,615,049 B2 * | 11/2009 | West | A61B 18/1492 606/41 |
| 8,137,337 B2 * | 3/2012 | Hakky | A61M 25/04 604/104 |
| 10,307,564 B2 * | 6/2019 | Erbey, II | A61M 25/10 |
| 11,298,506 B2 * | 4/2022 | Porter | A61M 25/0068 |
| 2003/0130610 A1 * | 7/2003 | Mager | A61M 25/0029 604/7 |
| 2005/0033265 A1 * | 2/2005 | Engel | A61M 25/0023 604/523 |
| 2005/0154386 A1 * | 7/2005 | West | A61B 18/1492 606/41 |
| 2007/0250035 A1 * | 10/2007 | El-Nounou | A61M 25/0082 604/509 |
| 2011/0245766 A1 * | 10/2011 | Leonard | A61M 25/10 604/103.01 |
| 2012/0253295 A1 * | 10/2012 | Nentwick | A61M 25/01 29/402.01 |
| 2014/0058316 A1 * | 2/2014 | Gupta | A61M 1/285 604/29 |
| 2014/0257013 A1 * | 9/2014 | D'Andrea | A61N 5/1071 600/2 |
| 2019/0030280 A1 * | 1/2019 | Yokoyama | A61M 25/0102 |

OTHER PUBLICATIONS

Vetter et al., "Total Replacement of the Mitral Apparatus With a Stentless, Chordally Supported Mitral Valve Allograft: an Experimental Study", J. Thorac Cardiovasc Surg, 1996, pp. 595-604, vol. 111.

* cited by examiner

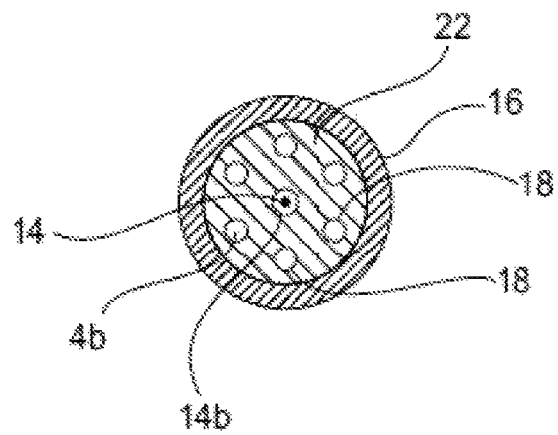 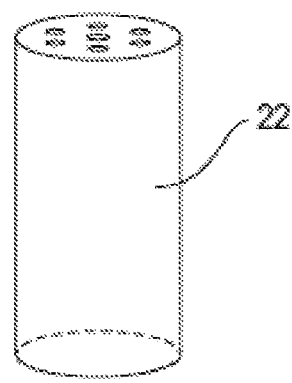
FIG. 3A  FIG. 3B
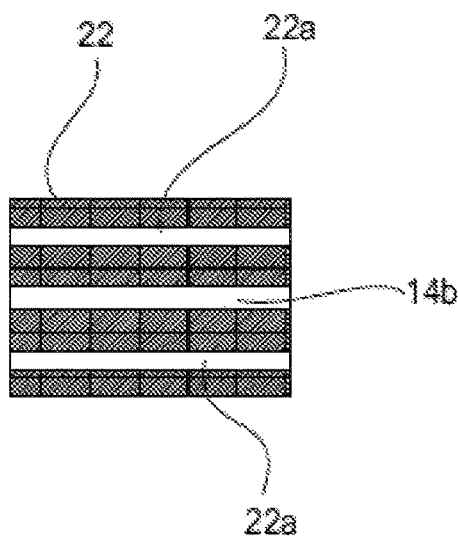 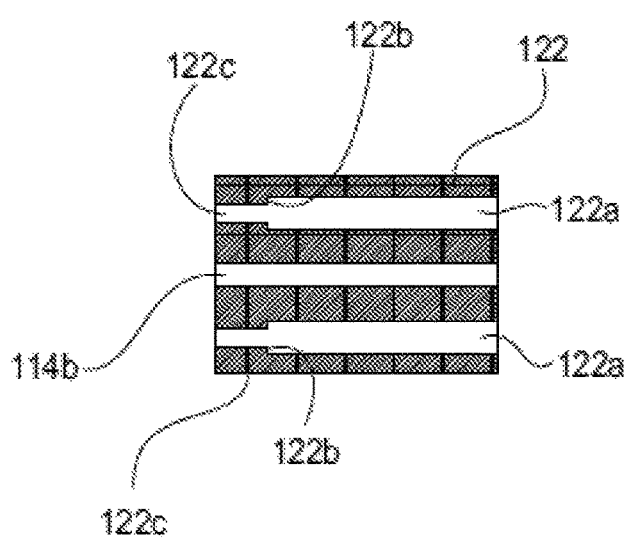
FIG. 3C  FIG. 3D

EXPANDABLE PERCUTANEOUS CANNULA

CROSS REFERENCE TO RELATED APPLICATIONS

This application is the United States national phase of International Application No. PCT/US2018/017795 filed February 12. 2018, and claims the benefit of U.S. Provisional Patent Application No. 62/458,234 filed Feb. 13, 2017, which is incorporated herein by reference.

Conventional cardiac surgery requiring cardiopulmonary bypass involves median sternotomy and cannulation of the ascending aorta and the right atrium (RA). The RA may be cannulated through the right atrial appendage with a single stage cannula directed to the inferior vena cava (IVC). Minimally invasive cardiac surgery may be performed with a single stage or multistage venous cannula inserted via open cut down or percutaneous approach to the common femoral vein and introduced into the RA using Seldinger techniques. At the time of minimally invasive aortic or mitral valve surgery, inadequate drainage from a single femoral venous cannula may often occur due to retraction needed to perform valve surgery or displacement or both. This often necessitates the need for an additional venous cannula to be placed. An adaptive technique applied with increasing frequency at the time of minimally invasive cardiac surgery is the use of bicaval drainage by placing a venous cannula from the common femoral vein into the RA and placement of a separate percutaneous cannula via the right internal jugular into the superior vena cava (SVC). In addition, a straight catheter configuration for venous cannulae, even if multistaged or with multiple drainage holes, does not allow for an efficient infilling of a cavity with a roughly spherical shape such as an atrium. This inefficiency is principally due to inadequate size and number of drainage holes to accommodate the volume or due to collapse of the chamber over the holes when vacuum is applied to facilitate drainage.

Extracorporeal membrane oxygenation (ECMO) is used with increasing frequency to manage complex patients with end-stage or acute respiratory or circulatory failure. The venous cannulae used for this application are similar if not identical to those used at the time of minimally invasive cardiac surgery due to limited variety of options. The need for heparin bonded/coated or "carmeda" coating is important to minimize thrombogenicity. As these are often placed percutaneously via femoral or internal jugular puncture, future cannula design requires ease of insertion, single cannula venous drainage performance to fully support the circulation with minimal impact on drainage with cardiac manipulation or retraction, and ease of removal.

Improved tools for use in minimally invasive cardiac surgery, such as minimally-invasive aortic or mitral valve surgery, are needed.

SUMMARY

A percutaneous cannula device is provided. The device, according to one aspect, comprises: an elongated member, such as a tube, having a proximal end, a distal end, a wall defining a lumen or passageway, and a longitudinal axis; an actuator, e.g., a guide wire, extending within the passageway of the elongated member from the proximal end of the elongated member to beyond the distal end of the elongated member; a head unit attached to and extending from a distal end of the elongated member, comprising: three or more flexible tubes, each flexible tube having a wall, a lumen, a proximal end, a distal end, and a plurality of holes extending through the wall of one or more of the three or more flexible tubes; a first spacer affixed to a distal end of the actuator and affixed to distal ends of the three or more flexible tubes, and spacing the flexible tubes in a pattern around the actuator; and a second spacer proximal to the first spacer, affixed to the distal end of the elongated member, comprising a guide through which the actuator passes, and retaining the three or more flexible tubes in a pattern around the actuator; and a closed fluid path defined by at least the flexible tubes and extending to an outlet from the device to which suction can be applied to draw fluid through the holes of the flexible tubes, through the flexible tubes, and through the outlet. Movement of the actuator in a proximal direction along the longitudinal axis of the elongated member moves the first spacer from a first, unexpanded position in which the flexible tubes at a point between the first spacer and the second spacer have a first distance from a point, such as a center point, between the flexible tubes (e.g., equidistant from each of the flexible tubes, or alternatively from the actuator at a point between the first spacer and the second spacer, such as at a point equidistant from the first spacer and the second spacer), and a second, expanded position in which the second spacer is closer to the first spacer, resulting in increased flexion of the flexible tubes away from the center point between the flexible tubes, such that a point on one or more of the flexible tubes has a second distance from the center point that is at least five times larger than the first distance from the center point.

Also provided herein is a method of draining a fluid from a site in a patient. According to one aspect, the method comprises inserting the device as described above, and throughout, with the head unit at a site in a patient; drawing the actuator toward the proximal end of the device, thereby expanding the head unit at the site in the patient; and applying a vacuum to the outlet of the device, thereby draining fluid present at the site of the patient.

BRIEF DESCRIPTION OF THE DRAWINGS

The drawings provided herein are schematic in nature, and their corresponding descriptions are provided for illustrative purposes only. Drawings are not necessarily to scale, and are scaled to illustrate various elements of aspects or embodiments of the devices described herein.

FIGS. 3A-3E depict various aspects of the second spacer as described herein.

DETAILED DESCRIPTION

Figure 1:
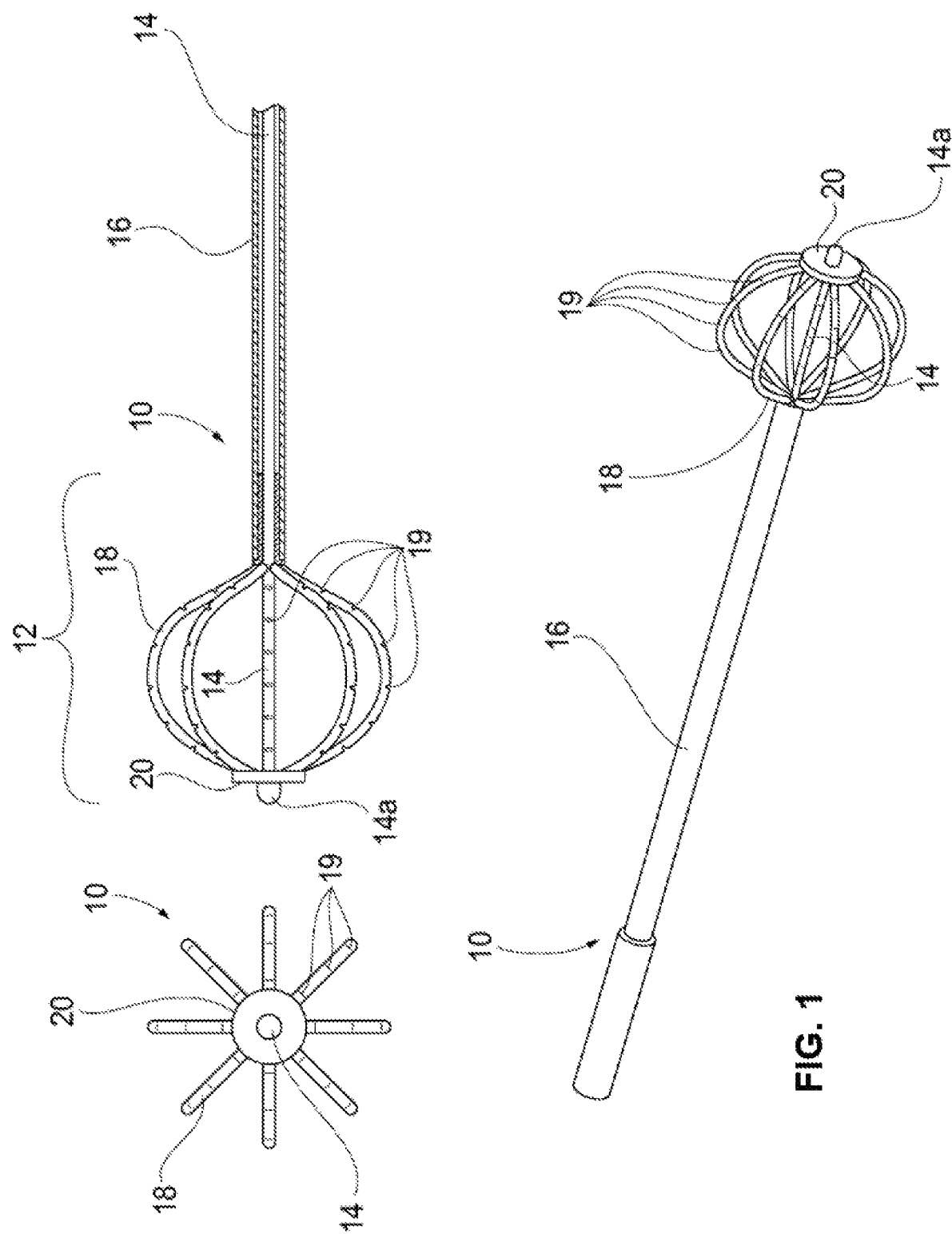
FIG. 1 provides various views of one aspect of the device described herein.

As used herein, spatial or directional terms, such as "left", "right", "inner", "outer", "above", "below", and the like, relate to the invention as it is shown in the drawing figures. However, it is to be understood that the invention can assume various alternative orientations and, accordingly, such terms are not to be considered as limiting. Further, as used herein, all numbers expressing dimensions, physical characteristics, processing parameters, quantities of ingredients, reaction conditions, and the like, used in the specification and claims are to be understood as being modified in all instances by the term "about". Accordingly, unless indicated to the contrary, the numerical values set forth in the following specification and claims may vary depending upon the desired properties sought to be obtained by the present invention. At the very least, and not as an attempt to limit the application of the doctrine of equivalents to the scope of the claims, each numerical value should at least be construed in light of the number of reported significant digits and by applying ordinary rounding techniques. Moreover, all ranges disclosed herein are to be understood to encompass the beginning and ending range values and any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 3.3, 4.7 to 7.5, 5.5 to 10, and the like. Additionally, all documents, such as, but not limited to, issued patents and patent applications, referred to herein are to be considered to be "incorporated by reference" in their entirety.

Further, as used herein, the terms "formed over", "deposited over", or "provided over" mean formed, deposited, or provided on but not necessarily in contact with the surface. For example, a coating layer "formed over" a substrate does not preclude the presence of one or more other coating layers or films of the same or different composition located between the formed coating layer and the substrate. Likewise, the terms "under" or "between" in the context of specified coating layers does not preclude the presence of one or more other coating layers or films of the same or different composition located between the recited layers.

The terms "distal" and "proximal" refer to directions with respect to the devices described herein (see, e.g., directions "D" and "P" in FIG. 2A), and although they also correspond to the relative position, orientation, and/or direction of element(s) of the devices described herein with respect to the end use of the device in typical use as a percutaneous cannula, those descriptors are provided only to describe the relative position, orientation, and/or direction of element(s) of the devices described herein with regard to the device as a whole, and to elements thereof, and do not require or infer that the elements are located, positioned, oriented, or in any physical relationship with an end user at any given time. Figures are not drawn to scale, but are drawn in a manner to best depict the relationship between the various elements of the device drawn in the figure.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

Provided herein is a percutaneous expandable venous cannula that may be easily inserted, for example, using standard Seldinger technique via the right internal jugular. It may be introduced into the superior vena cava then right atrium and directed into the inferior vena cava. Once inserted into position, the mechanism of action and design of the cannula allows it to be unsheathed to deliver several multi-pronged and multi-holed limbs that softly fill the right atrium to facilitate complete drainage, enable retraction of the chamber in surgery and mitigate suction occlusion. It assumes an ellipsoidal or spherical shape which fills the entire atrium, therefore, allowing for a more efficient and quick emptying of the chamber. When use is complete, the catheter is simply re-sheathed and withdrawn using known techniques for managing central venous catheters.

The primary use for this cannula is to facilitate minimally-invasive aortic or mitral valve surgery with single placement via the right internal jugular as the sole cannula needed for full support. The cannula can be heparin coated (e.g., Carmeda-coated), for example, for use for ECMO support.

One aspect of the device is depicted schematically in FIG. 1. An expandable vacuum port enabled bundle of equidistant plastic tubing slipped over a movable flexible stainless steel pull rod is constrained, and forced to expand due to the resistance of a second flexible stainless steel anchor rod at the bundle's trailing end. The resultant equidistant tubing expanded shape provides a series of vacuum ports along each tube and provides sufficient force to constrain the heart chamber (e.g., right atrium), as well as to remove blood. The bundle can then be collapsed and re-sheathed for extraction after the procedure.

In detail, FIG. 1 depicts various views of one aspect of the percutaneous cannula device 10 described herein, depicting head unit 12 in an expanded state. As depicted in FIG. 1, a guide wire 14 is located within a first tube 16 that can be described as a cannula. The guide wire 14 is any suitable guide wire or deformable, steerable wire as are broadly-known, for example, in the angioplasty, and more broadly in the vascular access, coronary intervention, and percutaneous arts, such as a stainless steel or NITINOL wire, that is optionally coated with a suitable polymer or other composition (for example and without limitation, ChoICE™, MAGIC TORQUE™, or any other of the large variety of guidewires available from Boston Scientific Corporation, or custom guidewires, such as, without limitation, GLIDEWIRE ADVANTAGE®, from Terumo Interventional Systems of Somerset, New Jersey).

Figure 2A:
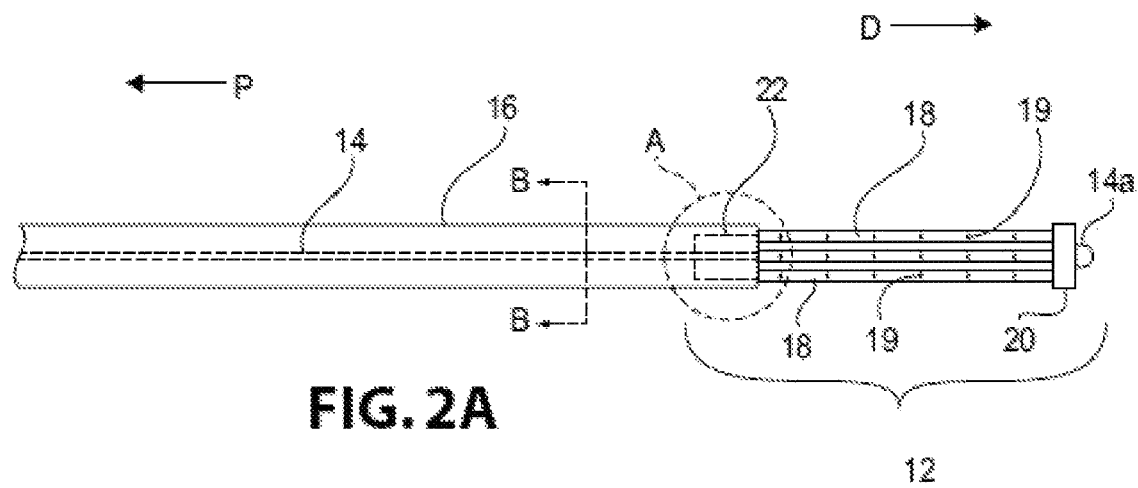
FIGS. 2A-2D depict various views of one aspect of the device described herein.
Figure 2B:
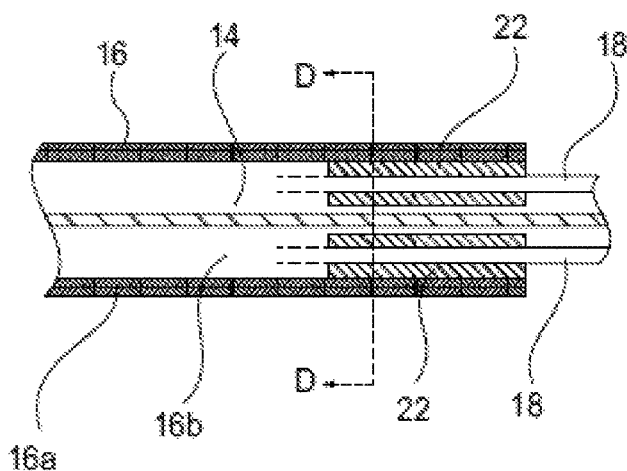

In use, the guide wire 14 slides within the tube 16, and is used both to direct and deploy the catheter through a patient's cardiovascular system, and, as described in further detail below, to cause expansion and contraction of the head unit 12 of the device 10 by moving the guide wire 14 along a longitudinal axis of the first tube 16. In an alternate aspect (not shown), one or more additional wires are enclosed within, or external to the tube 16 in order to assist in guidance of the device during deployment, and in another aspect, the guide wire 14 is used only to expand and contract the head unit 12, and one or more additional guide wires are used to guide the device. FIG. 2A depicts the distal end of the device 10, showing the head unit 12 in an un-expanded or contracted state used during storage, deployment and retraction of the device 10. As shown in FIG. 2B, the first tube has an inner wall 16a, which defines a lumen 16b, e.g., as shown in FIG. 2B. For the first tube 16, in various aspects of the invention, tubing is used. The tubing can be any tubing that is suitable for the described use, and a large variety of medical or biopharmaceutical grade tubing of varying diameters, thicknesses, and flexibility, such as fluoropolymer (e.g., PTFE, polytetrafluoroethylene), polyethylene, polyvinyl (e.g., PVC), silicone, and TYGON®, including impregnated tubing, such as silver-impregnated tubing, as are broadly-available, for example and without limitation, from US Plastic Corporation of Lima, Ohio. The tubing optionally comprises, at least in part, an anticoagulative coating, such as a CBAS® Heparin Surface (CARMEDA® BioActive Surface) coating.

Figure 2C:
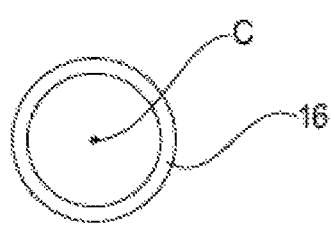
Figure 2D:
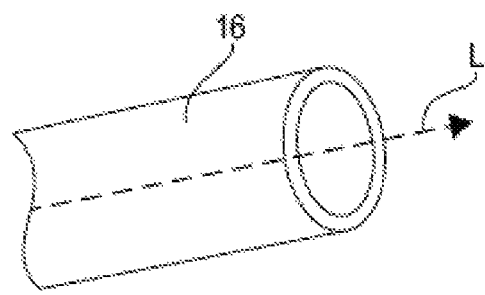

In use, the head unit 12 expands from a compressed or non-expanded state (FIG. 2A) in a direction normal to a longitudinal axis of the device L to an expanded state (FIG. 1). The longitudinal axis is an axis passing through a center point C of the lumen of the first tube 16, as shown in FIG. 2C, which, in reference to FIG. 2A, shows a cross section B on a plane normal to the longitudinal axis L of the device 10 (see also FIG. 2D). The guide wire 14 is configured substantially parallel to the longitudinal axis L. In use, the first tube 16 bends, and, as such, the longitudinal axis is not necessarily linear, but bends with the first tube 16 or any referenced portion of the device 10.

The head unit 12 comprises three or more flexible tubes 18, having perforations 19 in their walls through which liquid can flow at least when the head unit 12 is in an expanded state as shown, e.g., in FIG. 1. The perforations 19 may have any useful geometric shape, such as pores or cuts in the wall of the flexible tubes 18, that optionally expand when the tubes 18 are bent when transitioning the head unit 12 from an unexpanded to an expanded state. For example, cuts in the wall of a tube 18 will enlarge when the tube 18 is bent when transitioning the head unit 12 from an unexpanded to an expanded state. The perforations 19 may be placed on any side of the flexible tubes, e.g., facing the guide wire 14, facing other flexible tubes 18, facing outward opposite, or away from the guide wire 14, or in any direction therebetween, and/or in any combination thereof, so long as when the head unit 12 is in its expanded state, one or more perforations 19 in one or more, or all, flexible tubes 18 is open, permitting fluid passage from external to the flexible tube 18 into the lumen of the flexible tube 18.

The distal ends of the flexible tubes 18 and the distal end of the guide wire 14a are affixed to a first spacer 20, which is movable, and moves relative to tube 16 when the guide wire 14 is moved longitudinally (along the longitudinal axis) within tube 16. The proximal ends of tubes 18 are affixed to a distal end of tube 16, such that pulling the guide wire 14 in a proximal direction results in movement of the first spacer 20 towards tube 16, resulting in flexion of flexible tubes 18, and expansion of head unit 12 (FIG. 1), and movement of the first spacer in a distal direction when the head unit 12 is in an expanded state, results in a contraction of the head unit 12 towards a non-expanded state (FIG. 2A).

The first spacer 20 is affixed to a distal end of the guide 14 and the tubes 18, typically spacing tubes evenly about the device. The guide 14 and tubes 18 can be affixed to the first spacer 20 by any method, for example, by gluing. In one aspect, the first spacer 20 is a silicone plug prepared by applying silicone to the distal end of the guide 14 and tubes 18.

The head unit 12 also comprises a second spacer 22 proximal to the first spacer 20, and affixed to the tubes 18, and having a passage through which the guide 14 passes and can move in a longitudinal direction. Like the first spacer 20, the second spacer 22 spaces the flexible tubes 18 in a pattern around the guide 14, for example, substantially evenly about the guide 14, such that movement of the guide 14 in a proximal direction along the longitudinal axis of the first tube moves the first spacer 20 from a first, unexpanded position in which the flexible tubes 18 have a first distance from the guide 14, and a second, expanded position in which the first spacer 20 is closer to the second spacer 22, resulting in increased flexion of the flexible tubes 18 such that they have a second distance from the guide 14 that is larger than the first distance from the guide 14, e.g., at least 5, 10, or 20 times larger than the first distance from the guide 14. The second spacer 22 can be any useful composition, such as silicone.

Figure 3E:
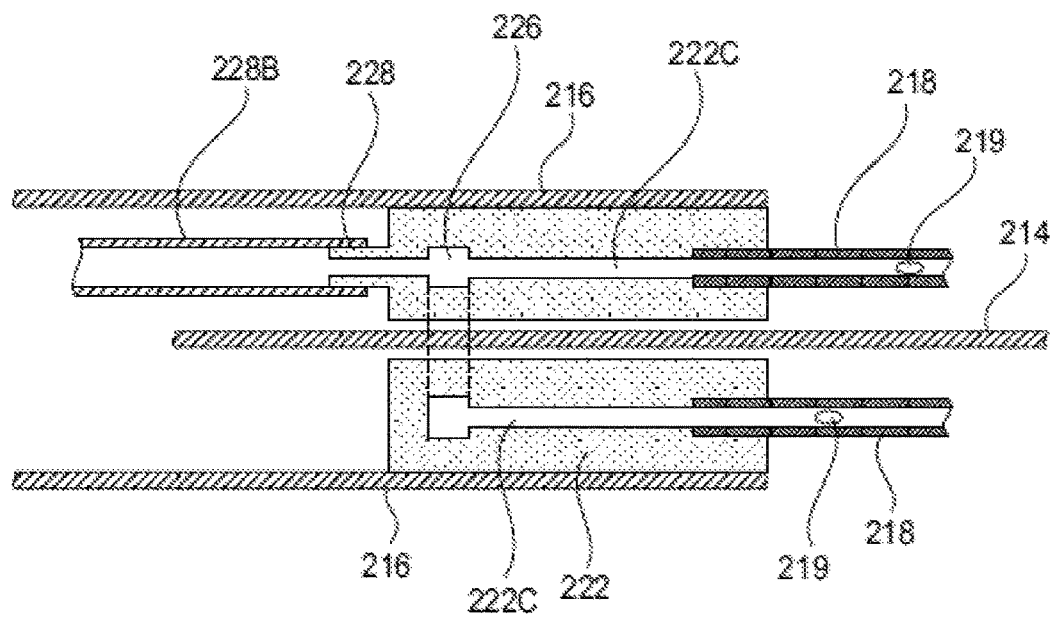
Figure 5:
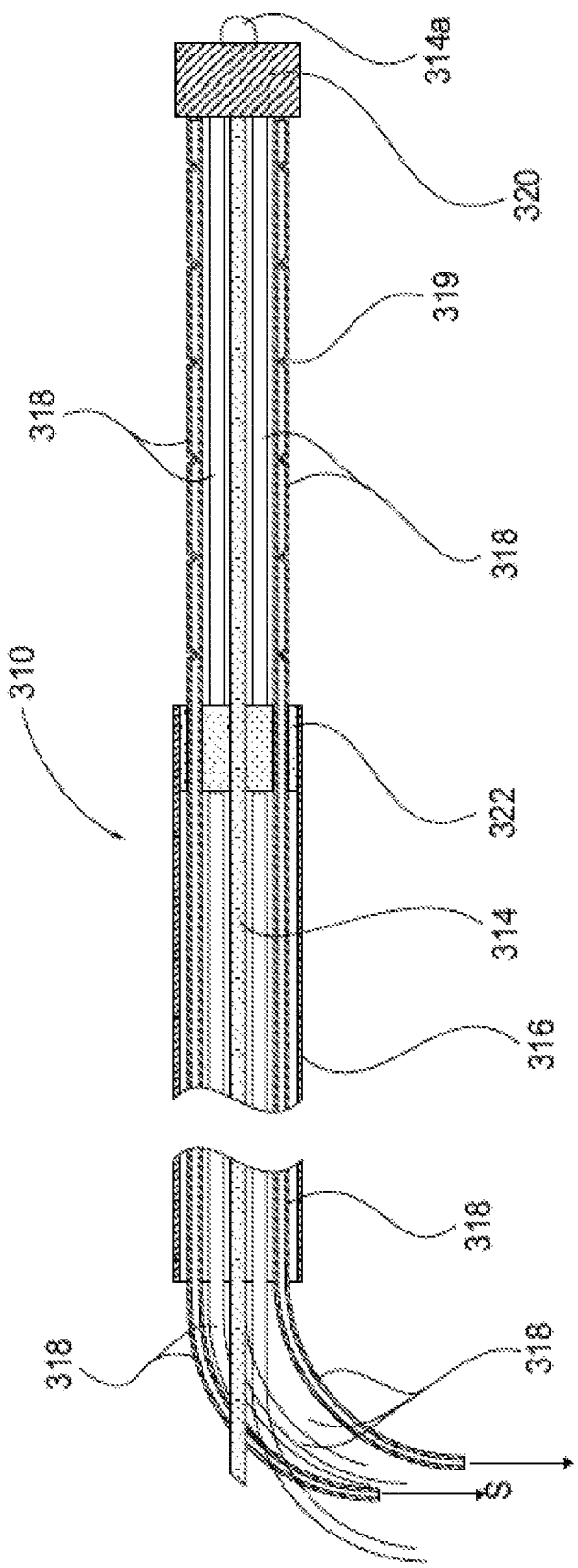
FIG. 5 is a cross sectional view of one aspect of the device described herein.

The flexible tubes 18 each have a lumen (central cavity) and either connect directly or indirectly through a closed fluid path to an outlet to which suction can be applied, and through which fluid, such as blood, can be drawn when a vacuum (suction) is applied to the outlet. By a closed fluid path, it is meant a conduit to which suction can be applied at the outlet, and fluid can be drawn into the fluid path, through the fluid path, and through the outlet with minimal or no loss of the fluid along the closed path, e.g., with no substantial leaks that interfere with drawing a fluid through the closed fluid path, such as substantial leaks in the fluid path. In one aspect, the proximal ends of the flexible tubes 18 are located at the second spacer 22, as illustrated in FIG. 3D, and in another aspect, the flexible tubes 18 continue further in a proximal direction party or fully through the tube 16, and in one aspect, as shown in FIG. 5, described below. In FIG. 5, the flexible tubes 318 pass out of the proximal end of the tube 316, forming an outlet of the device, and can be connected to a suction device, optionally via a manifold, which is a device where, e.g., the lumen of two or more flexible tubes (e.g., 18 or 318), e.g., all tubes (e.g., 18 or 318) in the device, are joined in a common cavity. Of note, in aspects where the proximal ends of the flexible tubes (e.g., 18 or 318) extend past the first spacer, those tubes have no perforations proximal to the spacer, unless the perforations are otherwise fluidly connected in a closed path via an outlet to a suction device, or a tube or manifold connected to, or for connection to the suction device. When suction is applied to a proximal end of the flexible tubes (e.g., 18 or 318), fluids, such as blood can be sucked from the holes (e.g., 19 or 319) in the tube (e.g., 18 or 318) at the head unit (e.g., 12 or 312), through the lumen (e.g., 16b or 316b) of the tube (e.g., 16 or 316), and out of a distal end of the device. As such, a closed, or contiguous, fluid path is present from the holes (e.g., 19 or 319), through the flexible tubes (e.g., 18 or 318), and extending out of a proximal end of the device (e.g., 10 or 310), forming an outlet and permitting a vacuum to be applied to a proximal end of the closed fluid path with insubstantial and preferably no loss of suction or leakage along the closed fluid path. To this end, the flexible tubes (e.g., 18 or 318) extend from the first spacer (e.g., 20 or 320) through the tube (e.g., 16 or 316), and out of the proximal end of the device (see FIG. 5, below). Referring to FIG. 1, as would be readily appreciated by one of ordinary skill in the art, the topology of the closed fluid path between the lumen of the flexible tubes 18 in the head unit 12, including the configuration of the second spacer 22, can vary greatly—so long as it permits removal by suction of fluid external to the flexible tubes 18 in the head unit 12 through the perforations 19 in the flexible tubes 18. In one aspect, the second spacer 22 comprises internal passages that connect the lumen of the flexible tubes 18 to a single, common passage. An example of such a second spacer 22 is shown in cross section in FIGS. 3D and 3E, described below.

Suction is applied to the device by any useful mechanism or device, such as by use of a medical syringe, a pump, a peristaltic pump, connection to a vacuum source, such as a vacuum system with a suitable trap for collecting fluid, or any other method.

FIG. 3A shows a cross section of the device across D in reference to FIG. 2B. The tube 16 is shown, with second spacer 22 inserted in the lumen thereof, and either friction-fitted, glued, or otherwise affixed within the tube 16. FIG. 3B provides an elevation view of one example of a second spacer 22 to insert into a distal end of tube 16. In one aspect, the flexible tubes 18 pass through the second spacer 22, to extend in a proximal direction beyond the second spacer 22 as shown in FIG. 5, described below. As shown in cross section in FIG. 3C, the second spacer 22 includes a passage 14b through which guide wire 14 passes as described elsewhere herein. In that aspect, passages 122a are essentially uniform over their length so that flexible tubes 18 can pass through the second spacer 22. In another aspect, the proximal ends of the flexible tubes 18 end at the second spacer, which is depicted in FIG. 3D, includes passages 122a for accepting a proximal end of each flexible tube 118 (six in reference to FIGS. 3A and 3B), and a stop or seat 122b for limiting passage of the tube through second spacer 122. Passages 122c extend the closed fluid path from the tubes 118 through the second spacer 122. For the second spacer, aspects depicted in FIGS. 3C and 3D, each flexible tube 118 can be friction-fitted, glued, heat welded, or otherwise affixed within the passage 122a of the second spacer 122. In reference to either aspect depicted in FIGS. 3C and 3D, second spacer 22, 122 includes a guide wire passage 14b, 114b through which the guide wire (e.g., 14 in FIG. 1, not shown) passes. Referring to FIG. 3C, but equally applicable to other aspects of the device described herein, the diameter of the guide wire 14 is smaller than that of the passage 14b so that the guide wire 14 can be moved within the passage 14b to expand or contract the head unit. In one aspect, the diameter of the passage 14b is the same or slightly larger than that of the guide wire 14 to produce a desired amount of friction between the second spacer 22 and the guide wire 14 to restrict the guide wire from freely moving within the passage 14b during use, without application of an external force on the guide wire 14 in a longitudinal direction. In another aspect, the diameter of the passage 14b is larger than that of the guide wire 14 so that the guide wire 14 can move freely within the passage 14b, in which case, longitudinal motion of the guide wire 14 through the passage 14b can be optionally restricted by any other means, at another position within the device 10, for example, by a friction fitting, a clamp, a solenoid, or a clip.

FIG. 3E depicts in cross section an alternative aspect of second spacer 222, inserted within tube 216, with guide wire 214, and flexible tubes 218 having perforations 219, all shown attached. The second spacer 222 includes fluid passages 222c connecting lumen of flexible tubes 218 to a common, annular passage 226 (shown in part in phantom) in which fluid from all flexible tubes 218 passes, and is drained through a single, common outlet 228 into a single drainage tube 228b for connection to a suction device (not shown), such as a pump, a bulb, a medical syringe, or any other useful device. The second spacer 22, 122, 222 can be 3D printed using any suitable material. Drainage tube 228b passes out the proximal end of tube 216, and is attached to a suction device.

In reference to FIG. 1, but equally applicable to other aspects of device, it should be noted that at any point at or proximal to the second spacer 22, within the tube 16, or proximal to the tube 16 (that is, extending past the proximal end of tube 16), the fluid paths (lumen or central cavities) of two or more, or all of the flexible tubes 18, can be joined using appropriate fittings.

When in an expanded state, e.g., as shown in FIG. 1, the device 10 not only expands tissue surrounding the head unit 12 as is necessary, but is used to drain liquid present in the space surrounding, or created by, the expanded head unit 12. The liquid is drained in a closed fluid path extending from the perforations 19 to any point proximal to the tube 16 or device 10, as depicted. A closed fluid path permits application of a vacuum (suction), e.g., from a pump, at the distal end of the tube 16 in order to suck liquid, such as blood, from the space containing and/or created by the expanded head unit 12.

Figure 4:
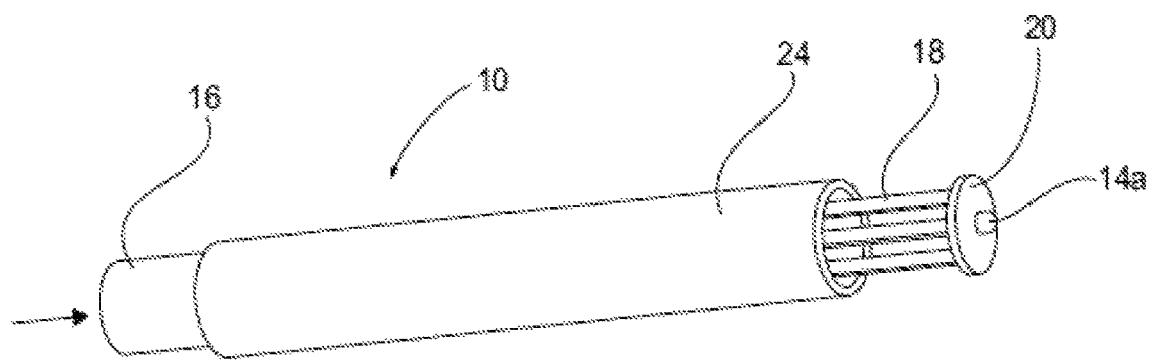
FIG. 4 shows one aspect of the device described herein, including a delivery sheath.

FIG. 4 depicts one aspect of a device 10, including tube 16, first spacer 20, flexible tubes 18, and distal end of guide wire 14a. The device 10 further includes a delivery sheath 24 into which the tube and head unit are inserted for delivery of the device 10, for example, by the Seldinger technique.

FIG. 5 depicts a further aspect of the device 310 described herein, comprising a guide wire 314, a tube 316, a first spacer 320, flexible tubes 318, perforations 319, and second spacer 322, wherein the flexible tubes 318 pass through the second spacer 322, for example, as described in the context of FIG. 3C, and out of a proximal end of tube 316, for connection directly to a syringe, such as a medical syringe, a pump, a vacuum system, or any other useful device to provide suction (S) to the flexible tubes 318 to draw liquid into the flexible tubes 318 through the perforations 319 and out of the flexible tubes 318 at their proximal ends as depicted. Proximal ends of the flexible tubes 318 are connected to a suction device by any useful means, such as by a manifold or a tubing connector, such as, for example and without limitation, any slip (friction) or threaded luer-type connector, as are broadly-known in the medical arts.

Any element of any aspect of the devices described herein may be prepared from a material having anti-thrombogenic qualities and/or includes an anti-thrombogenic coating on a blood-contacting surface thereof, so as to prevent or reduce the formation of clots during use of the device in a patient. An example of an anti-thrombogenic coating is a heparin bonded/coated surface, or "CARMEDA®" coating.

In one aspect, the catheter is a bundled cylinder of 1.8 mm diameter medical grade polyvinyl(PVC) tubing. A length of PVC tubing is slid onto the appropriate diameter stainless steel rod, and this assembly is attached to a small fixture. A series of slices are cut perpendicular to the center line of the tubing. As the tuning bundle expands, those slices open, allowing for the pull of a vacuum along the entire tube length. In aspects, the bundle is UV cure adhesive-anchored to a 3 mm thick PTFE cylinder at the leading end which provides initial equidistant spacing of the tubes making up the bundle and seals the tube ends. A second 3 mm thick TEFLON™ cylinder is used at the trailing end of the bundle to provide the same equidistant spacing of the tubes making up the bundle and control the expansion length of the catheter. The leading end of the resultant bundle is UV cure adhesive-bonded together at the TEFLON™ spacer. The trailing end bundle is also UV cure adhesive-bonded together at the TEFLON™ spacer. After the bundle is secured, a bendable stainless steel spring rod of 1.82 mm diameter is attached to the center of the leading end FTFE cylinder. This spring rod will be the force applicator to cause tube bundle expansion. The trailing end of the bundle at the TEFLON™ cylinder is free to move along the 1.82 mm stainless steel spring rod, and is attached using UV cure adhesive to the larger stainless steel spring rod which anchors the trailing end of the bundle. This combination allows the stiffer anchor spring rod to provide resistance to the trailing edge of the bundle, while the 1.82 mm diameter spring rod forces expansion of the tubing between the leading, and trailing bundles when pulled against the larger spring rod. After all UV cure adhesive is cured, the bundle is expanded, and subjected to a heat forming process that locks the bundle into its pre-determined equidistant expanded shape. After forming, the bundle is collapsed by pushing the 1.82 diameter spring rod. The entire bundle can then be placed in a larger diameter flexible tubing sheath for deployment by pushing the bundle out of the leading end of the deployment sheath at the correct position. The medical device mechanism of action is illustrated FIG. 2.

The device described herein provides for atrio-ventricular (AV) valve replacement and repair designed to occupy a volume as opposed to remove blood only from one extremity of the catheter, reducing invasiveness, operation times, and adapts to the atria volume.

In use, the catheter device according to any aspect described herein, is inserted into a blood vessel, such as a femoral vein or right jugular vein for insertion of the head unit into the right atrium of the heart in preparation for aortic valve repair or replacement, or in preparation for mitral valve repair or replacement performed via open or minimally invasive means, or for use for full extracorporeal membrane oxygenation.

The following numbered clauses describe various aspects of the invention:

1. A percutaneous cannula device, comprising:
   a. an elongated member, such as a tube, having a proximal end, a distal end, a wall defining a lumen or passageway, and a longitudinal axis;
   b. an actuator, e.g., a guide wire, extending within the passageway of the elongated member from the proximal end of the elongated member to beyond the distal end of the elongated member;
   c. a head unit attached to and extending from a distal end of the elongated member, comprising:
      i. three or more flexible tubes, each flexible tube having a wall, a lumen, a proximal end, a distal end, and a plurality of holes extending through the wall of one or more of the three or more flexible tubes;
      ii. a first spacer affixed to a distal end of the actuator and affixed to distal ends of the three or more flexible tubes, and spacing the flexible tubes in a pattern around the actuator; and
      iii. a second spacer proximal to the first spacer, affixed to the distal end of the elongated member, comprising a guide through which the actuator passes, and retaining the three or more flexible tubes in a pattern around the actuator; and
   d. a closed fluid path defined by at least the flexible tubes and extending to an outlet from the device to which suction can be applied to draw fluid through the holes of the flexible tubes, through the flexible tubes, and through the outlet.
2. The device of clause 1, wherein the guide is configured to apply friction to the actuator to restrict movement of the actuator in the direction of the longitudinal axis within the guide.
3. The device of clause 1, further comprising a delivery tube having a lumen, wherein at least a portion of the elongated member, the actuator, and the head unit are slidably-enclosed within the second tube and at least the head unit is configured to slide out of the delivery tube, allowing expansion of the flexible tubes beyond a diameter of the delivery tube.
4. The device of clause 1, wherein the elongated member is a flexible tube.
5. The device of clause 3, wherein the proximal ends of the flexible tubes end within the elongated member and/or within the second spacer, and are connected to the lumen of the elongated member, forming a closed fluid path having an outlet connected to a vacuum device, so that suction applied by the vacuum device to the outlet can draw blood through the holes of the flexible tubes, through the flexible tubes, through the elongated member, and through the outlet, e.g., into a container.
6. The device of any one of clauses 1-5, comprising six or more of the flexible tubes spaced about the actuator, for example from 6 to 12 of the flexible tubes spaced about the actuator, such as 6, 7, 8, 9, 10, 11, or 12 of the flexible tubes spaced about the actuator.
7. The device of any one of clauses 1-6, wherein the proximal ends of the flexible tubes extend from the elongated member forming the outlet connected to a vacuum device, so that suction applied by the vacuum device to the outlet can draw blood through the holes of the flexible tubes, through the flexible tubes, and through the outlet, e.g., into a container.
8. The device of clause 7, wherein the flexible tubes extend through the lumen of the elongated member and beyond a proximal end of the elongated member.
9. The device of clause 1, comprising a vacuum source attached to the outlet configured to apply suction to the outlet.
10. The device of clause 9, wherein the vacuum source is a vacuum chamber, a vacuum system, a pump, or a medical syringe.
11. The device of clause 9, further comprising a liquid trap between the outlet and the vacuum source, such as a trap.
12. A method of draining a fluid from a site in a patient, comprising:
    a. inserting the device of any one of clauses 1-11 with the head unit at a site in a patient;
    b. drawing the actuator toward the proximal end of the device, thereby expanding the head unit at the site in the patient; and
    c. applying a vacuum to the outlet of the device, thereby draining fluid present at the site of the patient.
13. The method of clause 12, further comprising after applying the vacuum:
    a. moving the actuator toward the distal end of the device, thereby contracting the head unit; and
    b. removing the device from the patient.
14. The method of clause 12 or clause 13, wherein the site of the patient is the right or left atrium of the heart of the patient.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments.

What is claimed is:

1. A percutaneous cannula device, comprising:
   a. a flexible, tubular elongated member having a proximal end, a distal end, a wall defining a lumen or passageway, and a longitudinal axis;
   b. an actuator extending within the passageway of the elongated member from the proximal end of the elongated member to beyond the distal end of the elongated member;
   c. a head unit attached to and extending from a distal end of the elongated member, comprising:
      i. three or more flexible tubes extending within the passageway of the elongated member, each flexible tube having a wall, a lumen, a proximal end, and a distal end;
      ii. a plurality of holes extending through the wall of one or more of the three or more flexible tubes;
      iii. a first spacer affixed to a distal end of the actuator and affixed to distal ends of the three or more flexible tubes, and spacing the flexible tubes in a pattern around the actuator; and iv. a second spacer proximal to the first spacer, affixed to the distal end of the elongated member, comprising a guide through which the actuator passes, and retaining the three or more flexible tubes in a pattern around the actuator; and d. a closed fluid path defined by at least the flexible tubes and extending to an outlet from the device to which suction can be applied to draw fluid through the holes of the flexible tubes, through the flexible tubes, and through the outlet.

2. The device of claim 1, wherein the guide is configured to apply friction to the actuator to restrict movement of the actuator in the direction of the longitudinal axis within the guide.

3. The device of claim 1, further comprising a delivery tube having a lumen, wherein at least a portion of the elongated member, the actuator, and the head unit are slidably-enclosed within the delivery tube and at least the head unit is configured to slide out of the delivery tube, allowing expansion of the flexible tubes beyond a diameter of the delivery tube.

4. The device of claim 3, wherein the proximal ends of the flexible tubes end within the elongated member and/or within the second spacer, and are connected to the lumen of the elongated member, forming a closed fluid path having an outlet connected to a vacuum device, so that suction applied by the vacuum device to the outlet can draw blood through the holes of the flexible tubes, through the flexible tubes, through the elongated member, and through the outlet.

5. The device of claim 1, comprising six or more flexible tubes spaced about the actuator, or from 6 to 12 flexible tubes spaced about the actuator.

6. The device of claim 1, wherein the proximal ends of the flexible tubes extend from the elongated member forming the outlet connected to a vacuum device, so that suction applied by the vacuum device to the outlet can draw blood through the plurality of holes extending through the wall of the one or more flexible tubes, through the flexible tubes, and through the outlet.

7. The device of claim 6, wherein the flexible tubes extend through the lumen of the elongated member and beyond a proximal end of the elongated member.

8. The device of claim 1, comprising a vacuum source attached to the outlet configured to apply suction to the outlet.

9. The device of claim 8, wherein the vacuum source is a vacuum chamber, a vacuum system, a pump, or a medical syringe.

10. The device of claim 8, further comprising a liquid trap between the outlet and the vacuum source.

11. A method of draining a fluid from a site in a patient, comprising:
a. inserting the device of claim 1 with the head unit at a site in a patient;
b. drawing the actuator toward the proximal end of the device, thereby expanding the head unit at the site in the patient; and
c. applying a vacuum to the outlet of the device, thereby draining fluid present at the site of the patient.

12. The method of claim 11, further comprising after applying the vacuum:
a. moving the actuator toward the distal end of the device, thereby contracting the head unit; and
b. removing the device from the patient.

13. The method of claim 11, wherein the site of the patient is the right or left atrium of the heart of the patient.

14. The device of claim 1, wherein the actuator comprises a plurality of holes.

15. The device of claim 1, wherein the holes in the flexible tubes are configured to expand as the head unit transitions from an unexpanded state to an expanded state.

16. The device of claim 1, wherein the holes in the flexible tubes face outward away from the actuator.

17. The device of claim 1, wherein the holes in the flexible tubes face the actuator.

18. A percutaneous cannula device, comprising:
a. a flexible, tubular elongated member having a proximal end, a distal end, a wall defining a lumen or passageway, and a longitudinal axis;
b. an actuator extending within the passageway of the elongated member from the proximal end of the elongated member to beyond the distal end of the elongated member;
c. a head unit attached to and extending from a distal end of the elongated member, comprising:
i. three or more flexible tubes extending within the passageway of the elongated member, each flexible tube having a wall, a lumen, a proximal end, and a distal end;
ii. a plurality of holes extending through the wall of one or more of the three or more flexible tubes;
iii. a first spacer affixed to a distal end of the actuator and affixed to distal ends of the three or more flexible tubes, and spacing the flexible tubes in a pattern around the actuator; and
iv. a second spacer proximal to the first spacer, affixed to the distal end of the elongated member, comprising a guide through which the actuator passes, and retaining the three or more flexible tubes in a pattern around the actuator; and
d. a closed fluid path defined by at least the flexible tubes and extending to an outlet from the device to which suction can be applied to draw fluid through the holes of the flexible tubes, through the flexible tubes, and through the outlet;
e. wherein the actuator comprises a plurality of holes.

* * * * *